US008097648B2

(12) United States Patent
Littlefield et al.

(10) Patent No.: US 8,097,648 B2
(45) Date of Patent: Jan. 17, 2012

(54) METHODS AND COMPOSITIONS FOR USE IN TREATING CANCER

(75) Inventors: Bruce A. Littlefield, Andover, MA (US); Murray J. Towle, Auburn, NH (US); Boris M. Seletsky, Andover, MA (US); Melvin J. Yu, Andover, MA (US); Wanjun Zheng, Londonderry, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 586 days.

(21) Appl. No.: 11/282,505

(22) Filed: Nov. 18, 2005

(65) Prior Publication Data
US 2006/0104984 A1    May 18, 2006

Related U.S. Application Data

(63) Continuation-in-part of application No. 10/687,526, filed on Oct. 16, 2003, which is a continuation of application No. 10/272,167, filed on Oct. 16, 2002, now Pat. No. 6,653,341, which is a continuation-in-part of application No. 09/843,617, filed on Apr. 26, 2001, now Pat. No. 6,469,182, which is a continuation of application No. 09/677,485, filed on Oct. 2, 2000, now Pat. No. 6,365,759, which is a continuation of application No. 09/334,488, filed on Jun. 16, 1999, now Pat. No. 6,214,865.

(60) Provisional application No. 60/089,682, filed on Jun. 17, 1998.

(51) Int. Cl.
*A61K 31/335* (2006.01)
(52) U.S. Cl. ...................................................... 514/450
(58) Field of Classification Search .................... 514/450
See application file for complete search history.

(56) References Cited

U.S. PATENT DOCUMENTS

| | | | |
|---|---|---|---|
| 5,338,865 | A | 8/1994 | Kishi et al. |
| 5,436,238 | A | 7/1995 | Kishi et al. |
| 6,214,865 | B1 | 4/2001 | Littlefield et al. |
| 6,365,759 | B1 | 4/2002 | Littlefield et al. |
| 6,469,182 | B1 | 10/2002 | Littlefield et al. |
| 6,653,341 | B1 | 11/2003 | Littlefield et al. |
| 7,470,720 | B2 | 12/2008 | Littlefield et al. |
| 2010/0190843 | A1 | 7/2010 | Agoulnik et al. |
| 2011/0172446 | A1 | 7/2011 | Littlefield et al. |

FOREIGN PATENT DOCUMENTS

| | | |
|---|---|---|
| EP | 0 572 109 A1 | 12/1993 |
| WO | WO 93/17690 | 9/1993 |
| WO | WO 2006/076100 | 7/2006 |
| WO | WO 2010/113984 | 1/2010 |

OTHER PUBLICATIONS

International Search Report from PCT/US2003/032711.

Aicher et al., "Total Synthesis of Halichondrin B and Norhalichondrin B," J. Am. Chem. Soc. 114:3162-3164 (1992).
Horita et al., "Synthetic Studies of Halichondrin B, an Antitumor Polyether Macrolide Isolated from a Marine Sponge. 8. Synthesis of the Lactone Part (C1-C36) via Homer-Emmons Coupling Between C1-C15 and C16-C36 Fragments and Yamaguchi Lactonization," Tetrahedron Letters 38:8965-8968 (1997).
Stamos et al., "New Synthetic Route to the C.14-C.38 Segment of Halichondrins," J. Org. Chem. 62:7552-7553 (1997).
Towle et al., "In Vitro and In Vivo Anticancer Activities of Synthetic Macrocyclic Ketone Analogues of Halichondrin B," Cancer Res. 61:1013-1021, 2001.
Supplementary European Search Report from European Patent Application No. 03776422.2, dated Aug. 4, 2009 (date of completion of search) and Aug. 12, 2009 (date of mailing of report).
Cigler and Vahdat "Eribulin mesylate for the treatment of breast cancer" Expert Opin. Pharmacother. 11: 1587, 2010.
Cortes et al. "Phase II study of the halichondrin B analog eribulin mesylate in patients with locally advanced or metastatic breast cancer previously treated with an anthracycline, a taxane, and capecitabine" J. Clin. Oncol. 28: 3922, 2010.
Twelves et al. "A phase III study (EMBRACE) of eribulin mesylate versus treatment of physician's choice in patients with locally recurrent or metastatic breast cancer previously treated with an anthracycline and a taxane." J. Clin. Oncol. 28:18s, 2010 (suppl; abstr CRA1004A).
Vahdat et al. "Phase II study of eribulin mesylate, a halichondrin B analog, in patients with metastatic breast cancer previously treated with an anthracycline and a taxane" J. Clin. Oncol. 27: 2954, 2009.
Agoulnik et al., "Sensitivity to halichondrin analog E7389 and hemiasterlin analog E7974 correlates with βIII tubulin isotype expression in human breast cancer cell lines," J Clin Oncol, 2005 ASCO Meeting Proceedings. vol. 23, No. 16S, Part I of II (Jun. 1 Supplement), 2005: 2012.
Arnold et al., "Phase II evaluation of eribulin mesylate (E7389, NSC 707389) in patients with metastatic or recurrent squamous cell carcinoma of the head and neck: Southwest Oncology Group trial S0618," Invest New Drugs, 29:352-359, 2009.
Beusterien et al., "Patient preferences for chemotherapies used in breast cancer," J Clin Oncol, 29:2011 (suppl; abstr e19667).
Blum et al., "Impact of the Number of Prior Chemotherapy Regimens on Overall Survival (OS) among Subjects with Locally Recurrent or Metastatic Breast Cancer Treated with Eribulin Mesylate: Results from the Phase III EMBRACE Study," Abstract No. P6-13-01 33$^{rd}$ Annual San Antonio Breast Cancer Symposium, San Antonio, TX, Dec. 8-12, 2010.
Budman et al., "Synergistic combinations of E7389 (Halichondrin B analogue) with conventional agents: in vitro median effect analysis in cell lines with potential clinical implications," Breast Cancer Research and Treatment, (2004) vol. 88, No. Suppl. 1, pp. S238-S239. Meeting Info: 27$^{th}$ Annual Charles A Coltman San Antonio Breast Cancer Symposium. San Antonio, TX, USA. Dec. 8-11, 2004, Abstract No. 6055.
Cortes et al., "Eribulin monotherapy versus treatment of physician's choice in patients with metastatic breast cancer (EMBRACE): a phase 3 open-label randomised study," Lancet, 377:914-923, 2011.

(Continued)

Primary Examiner — Andrew D. Kosar
(74) Attorney, Agent, or Firm — Clark & Elbing LLP

(57) ABSTRACT

The invention provides methods and compositions for use in treating diseases associated with excessive cellular proliferation, such as cancer.

5 Claims, No Drawings

OTHER PUBLICATIONS

CTEP Rapid Communication, Solicitation for Letter of Intent, Clinical trials, Preclinical experiments: E7389, Halichondrin B analog (NSC 707389), Nov. 1, 2005.

Das et al., "A phase II study of a novel anti-tubulin, E7389, in patients with advanced non-small cell lung cancer (NSCLC)," *J Clin Oncol*, (Jun. 20, 2006) vol. 24, No. 18, Part 1, Supp. [S], pp. 390S-390S, Abstract No. 7106.

de Bono et al., "Phase II study of eribulin mesylate (E7389) in patients (pts) with metastatic castration-resistant prostate cancer (CRPC) stratified by prior taxane therapy," Abstract No. 166, 2009 Genitourinary Cancers Symposium.

Elsayed et al., "Phase I study of a new Halichondrin B analog, E7389, administered by 1-hour IV infusion every 21 days," *Eur J Cancer Suppl* 2(8):163, Abstr No. 535, 2004.

Gitlitz et al., "A phase II study of the halichondrin B analog, E7389, in patients (pts) with advanced non-small cell lung cancer (NSCLC) previously treated with a taxane," *J Clin Oncol* 27:15s, Abstr. No. 535, 2004.

Gitlitz et al., "Notable progression free survival (PFS) and disease control rate (DCR) with the halichondrin B analogue eribulin mesylate in advanced non-small cell lung cancer (NSCLC) patients (pts) previously treated with a taxane," *J Thor Oncol*, 4:S450, 2009.

Goel et al., "A phase I study of halichondrin B analog E7389 in combination with gemcitabine in patients with refractory or advanced solid tumours," Abstract No. 417, 20th EORTC-NCI-AACR Symposium on Molecular Targets and Cancer Therapeutics, Geneva Switzerland Oct. 21-24, 2008.

Goel et al., "A phase I study of eribulin mesylate (E7389), a mechanistically novel inhibitor of microtubule dynamics, in patients with advanced solid malignancies," *Clin Cancer Res*, 15:4207-4212, 2009.

Hensley et al., "Eribulin mesylate (halichondrin B analog E7389) in platinum-resistant epithelial ovarian cancer (PR-EOC): A CTEP-sponsored phase II study," *J Clin Oncol*, 27:15s, 2009 (suppl; abstr 5561).

Lin and Burstein, "EMBRACE, eribulin, and new realities of advanced breast cancer," *Lancet*, 377:878-80, 2011.

Mani and Swami, "Eribulin mesilate, a halichondrin B analogue, in the treatment of breast cancer," *Drugs of Today*, 46:641-653, 2010.

Molife et al., "Phase II multicenter, two-stage study of E7389 in patients with hormone refractory prostate cancer with advanced and/or metastatic disease stratified by prior chemotherapy," *J Clin Oncol*, 2007 ASCO Annual Meeting Proceedings Part 1. vol. 25, No. 18S (Jun. 20 Supplement), 2007:15513.

Moore et al., "A phase II study of halichondrin B analog eribulin mesylate (E7389) as second-line therapy for patients with advanced pancreatic cancer," *J Clin Oncol*, 27, 2009 (suppl; abstr e15634).

Morris, "Advances in therapy: eribulin improves survival for metastatic breast cancer," *Anticancer Drugs*, 21:885-889, 2010.

Narayan et al., "Second generation eribulin analogs: Efficacy against multi-drug resistant tumors and brain tumors," Abstract No. 2704, 100th Annual Meeting of the American Association for Cancer Research, Denver, CO, USA, Apr. 18-22, 2009.

Quinn et al., "Phase II study of eribulin (halichondrin B analogue, E7389) in patients with advanced urothelial cancer (AUC)—California Cancer Consortium led NCI/CTEP-sponsored trial," EJC Supplements, (Sep. 2009) vol. 7, No. 2, p. 442.

Quinn et al., "Phase II study of eribulin (E7389) in patients (pts) with advanced urothelial cancer (UC)—Final report: A California Cancer Consortium-led NCI/CTEP-sponsored trial," *J Clin Oncol* 28:7s, 2010 (suppl; abstr 4539).

Schoffski et al. "Eribulin mesylate (E7389) in patients with leiomyosarcoma (LMS) and other (OTH) subtypes of soft tissue sarcoma (STS): a Phase II study from the European Organisation for Research and Treatment of Cancer—Soft Tissue and Bone Sarcoma Group (EORTC 62052)," EJC Supplements, (Sep. 2009) vol. 7, No. 2, pp. 591-591.

Schoffski et al. Activity of eribulin mesylate (E7389) in patients with soft tissue sarcoma (STS): Phase II studies of the European Organisation for Research and Treatment of Cancer Soft Tissue and Bone Sarcoma Group (EORTC 62052), *J Clin Oncol*, 28:15s, 2010 (suppl; abstr 10031).

Spira et al., "Phase II study of eribulin mesylate (E7389), a mechanistically novel inhibitor of microtubule dynamics, in patients with advanced non-small cell lung cancer (NSCLC)," *J Clin Oncol*, 2007 ASCO Annual Meeting Proceedings Part I. vol. 25, No. 18S (Jun. 20 Supplement), 2007: 7546.

Stein et al., "ECOG 5805: A phase II study of eribulin mesylate (E7389) in patients (pts) with metastatic castration-resistant prostate cancer (CRPC)," *J Clin Oncol*, 28:15s, 2010 (suppl; abstr 4556).

Swami et al., "Phase IB study of eribulin mesylate in combination with carboplatin in patients with advanced solid tumors," *J Clin Oncol*, 28: 15s, 2010 (suppl; abstr 2589).

Swami U, et al. Eribulin—A review of preclinical and clinical studies. Crit Rev Oncol/Hematol (2011), doi:10.1016/j.critrevonc.2011.03.002.

Synold et al., "A phase I pharmacokinetic and target validation study of the novel anti-tubulin agent E7389: A California Cancer Consortium trial," *J Clin Oncol*, 2005 ASCO Annual Meeting Proceedings, vol. 23, No. 16S (Jun. 1 Supplement), 2005: 3036.

Synold et al., "Phase I and pharmacokinetic (PK) study of eribulin (E7389) in patients (pts) with renal dysfunction (RD) and advanced urothelial cancer (UC): A California Cancer Consortium Trial," *J Clin Oncol*, 28:15s, 2010 (suppl; abstr 2527).

Tan et al., "Phase I study of eribulin mesylate administered once every 21 days in patients with advanced solid tumors," *Clin Cancer. Res*, 15:4213-4219, 2009.

Towle et al., "In vivo Efficacy of E7389, a Synthetic Analog of the Marine Sponge Antitubulin Agent Halichondrin B, Against Human Tumor Xenografts Under Monotherapy and Combination Therapy Conditions," Proceedings of the American Association for Cancer Research Annual Meeting, (Jul. 2003) vol. 44, pp. 539-540. 94th Annual Meeting of the American Association for Cancer Research, Washington, DC, USA, Jul. 11-14, 2003, Abstract No. 2749.

Wendling, "Eribulin Monotherapy Boosts Survival in Late Metastatic Disease," *The Oncology Report, Breast Cancer*, Jul./Aug. 2010, pp. 1-10.

Zhang et al., "Delineation of the interactions between the chemotherapeutic agent eribulin mesylate (E7389) and human CYP3A4," *Cancer Chemother Pharmacol*, 62:707-16, 2008.

METHODS AND COMPOSITIONS FOR USE IN TREATING CANCER

CROSS-REFERENCE TO RELATED APPLICATIONS

This application is a continuation-in-part of, and claims priority from, U.S. patent application Ser. No. 10/687,526, filed Oct. 16, 2003 (pending), which is a continuation of U.S. patent application Ser. No. 10/272,167, filed Oct. 16, 2002 (now U.S. Pat. No. 6,653,341), which is a continuation-in-part of, and claims priority from, U.S. patent application Ser. No. 09/843,617, filed Apr. 26, 2001 (now U.S. Pat. No. 6,469,182), which is a continuation of U.S. patent application Ser. No. 09/677,485, filed Oct. 2, 2000 (now U.S. Pat. No. 6,365,759), which is a continuation of U.S. patent application Ser. No. 09/334,488, filed Jun. 16, 1999 (now U.S. Pat. No. 6,214,865), which claims priority from U.S. Provisional Patent Application Ser. No. 60/089,682, filed Jun. 17, 1998 (now abandoned). The contents of the earlier filed applications are incorporated by reference herein in their entirety.

FIELD OF THE INVENTION

This invention relates to methods and compositions for use in treating cancer.

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches typically involve the administration of chemotherapeutic drugs that interfere with the growth of rapidly dividing cells, such as cancer cells.

Halichondrin B is a structurally complex, macrocyclic compound that was originally isolated from the marine sponge *Halichondria okadai*, and subsequently was found in *Axinella* sp., *Phakellia carteri*, and *Lissondendryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^S$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

SUMMARY OF THE INVENTION

The invention provides methods of inhibiting growth of tumors in patients, which involve administering to the patients a compound of the structure:

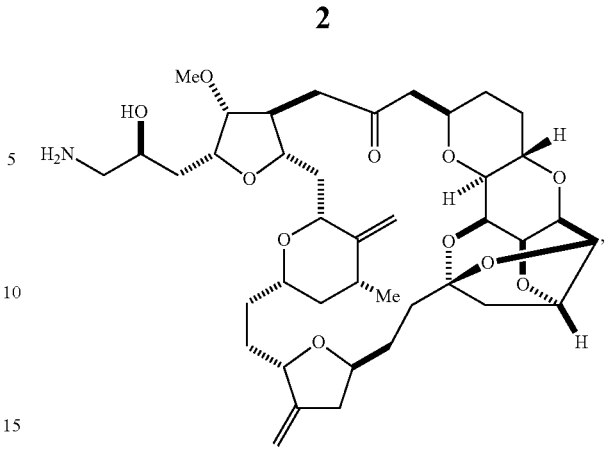

or a pharmaceutically acceptable salt thereof, wherein the tumor is breast carcinoma, and wherein the compound or pharmaceutically acceptable salt is not co-administered with another pharmaceutically active agent. The compound or pharmaceutically acceptable salt may be administered in a pharmaceutical composition including a pharmaceutically-acceptable carrier. The compound or pharmaceutically acceptable salt is administered, for example, by oral, topical, parenteral, or intravenous routes, or by injection or inhalation. Alternatively, the compound or pharmaceutically acceptable salt is administered in a controlled-release formulation.

The invention provides methods of treating cancer in patients, which involve administering to the patients a compound having the structure:

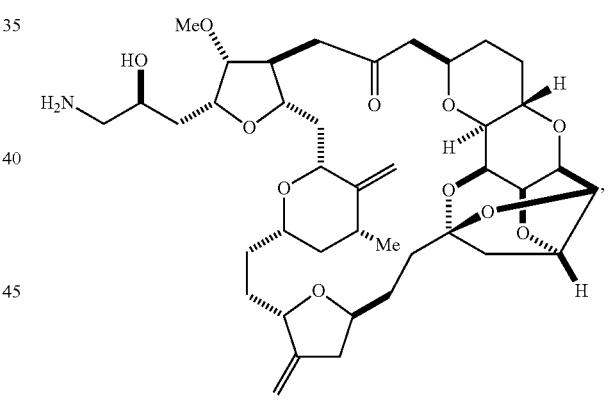

or a pharmaceutically acceptable salt thereof, in combination with one or more second anti-cancer agents selected from the group consisting of floxuridine, vinorelbine, and an antibody (e.g., a monoclonal antibody). In one example, the antibody is specific for HER-2/erb B2 (e.g., trastuzumab).

The methods of the invention can be used in the treatment of, for example, non-small cell lung cancer, breast cancer, colorectal cancer, pancreatic cancer, ovarian cancer, skin cancer, prostate cancer, cancer of the brain or nervous system, head and neck cancer, testicular cancer, lung cancer, liver cancer, kidney cancer, bladder cancer, gastrointestinal cancer, bone cancer, cancer of the endocrine system, cancer of the lymphatic system, fibrosarcoma, neurectodermal tumor, mesothelioma, epidermoid carcinoma, or Kaposi's sarcoma.

The methods of the invention can also include administration of one or more additional anti-cancer agents. For example, agents such as antimetabolites (e.g., methotrexate, purine antagonists (e.g., mercaptopurine, thioguanine, fludarabine phosphate, cladribine, or pentostatin), or pyrimidine antagonists (e.g., gemcitabine, capecitabine, fluorouracil, 5-fluorouracil, cytarabine, or azacitidine)), antibiotics (e.g., anthracyclines (e.g., doxorubicin, epirubicin, daunorubicin, or idarubicin), adriamycin, dactinomycin, idarubincin, plicamycin, mitomycin, or bleomycin), alkylating agents (e.g., procarbazine, dacarbazine, altretamine, cisplatin, carboplatin, or nitrosoureas), plant alkaloids (e.g., vinblastine, vincristine, etoposide, teniposide, topotecan, irinotecan, paclitaxel, or docetaxel), anticoagulants (e.g., heparin or warfarin), antibodies, biological agents (e.g., hormonal agents, cytokines, interleukins, interferons, granulocyte colony stimulating factor (G-CSF), macrophage colony stimulating factor (M-CSF), granulocyte macrophage colony stimulating factor (GM-CSF), chemokines, or vaccine antigens), and/or anti-angiogenic agents (e.g., angiostatin or endostatin) can be used.

The invention also provides compositions that include a compound having the structure:

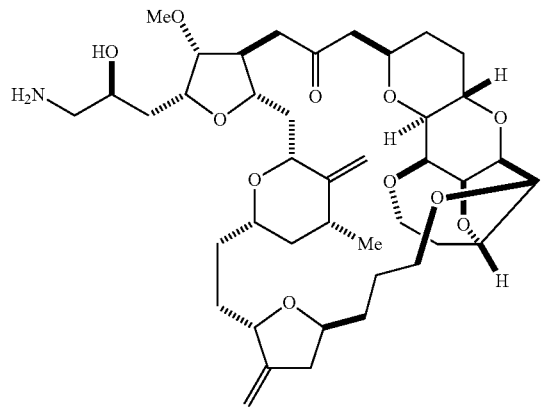

or a pharmaceutically acceptable salt thereof, in combination with one or more second anti-cancer agents selected from the group consisting of floxuridine, vinorelbine, and an antibody (e.g., a monoclonal antibody). In one example, the antibody is specific for HER-2/erb B2 (e.g., trastuzumab).

The compositions can include, optionally, one or more additional anti-cancer agents. For example, agents such as antimetabolites (e.g., methotrexate, purine antagonists (e.g., mercaptopurine, thioguanine, fludarabine phosphate, cladribine, or pentostatin), or pyrimidine antagonists (e.g., gemcitabine, capecitabine, fluorouracil, 5-fluorouracil, cytarabine, or azacitidine)), antibiotics (e.g., anthracyclines (e.g., doxorubicin, epirubicin, daunorubicin, or idarubicin), adriamycin, dactinomycin, idarubincin, plicamycin, mitomycin, or bleomycin), alkylating agents (e.g., procarbazine, dacarbazine, altretamine, cisplatin, carboplatin, or nitrosoureas), plant alkaloids (e.g., vinblastine, vincristine, etoposide, teniposide, topotecan, irinotecan, paclitaxel, or docetaxel), anticoagulants (e.g., heparin or warfarin), antibodies, biological agents (e.g., hormonal agents, cytokines, interleukins, interferons, granulocyte colony stimulating factor (G-CSF), macrophage colony stimulating factor (M-CSF), granulocyte macrophage colony stimulating factor (GM-CSF), chemokines, or vaccine antigens), and/or anti-angiogenic agents (e.g., angiostatin or endostatin) can be included in the compositions.

The invention further provides kits that include a compound having the structure:

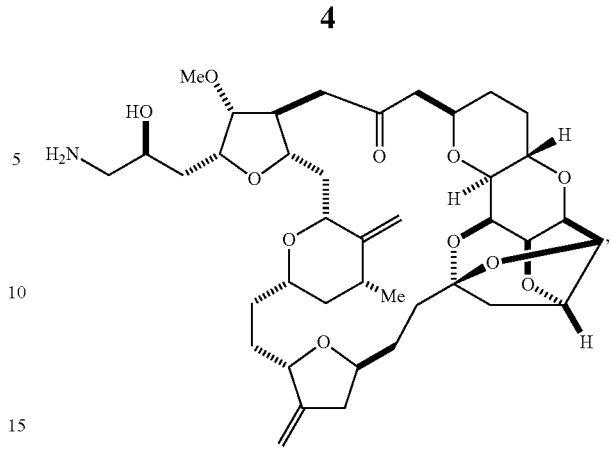

or a pharmaceutically acceptable salt thereof, and a second (or further) anti-cancer agent.

Second anti-cancer agents of the kits of the invention can be, for example, antimetabolites (e.g., methotrexate, purine antagonists (e.g., mercaptopurine, thioguanine, fludarabine phosphate, cladribine, or pentostatin), or pyrimidine antagonists (e.g., gemcitabine, capecitabine, fluorouracil, 5-fluorouracil, floxuridine, cytarabine, or azacitidine)), antibiotics (e.g., anthracyclines (e.g., doxorubicin, epirubicin, daunorubicin, or idarubicin), adriamycin, dactinomycin, idarubincin, plicamycin, mitomycin, or bleomycin), alkylating agents (e.g., procarbazine, dacarbazine, altretamine, cisplatin, carboplatin, or nitrosoureas), plant alkaloids (e.g., vinblastine, vincristine, etoposide, teniposide, topotecan, irinotecan, vinorelbine, paclitaxel, or docetaxel), anticoagulants (e.g., heparin or warfarin), antibodies (e.g., monoclonal antibodies and/or antibodies specific for HER-2/erb B2 (e.g., trastuzumab)), biological agents (e.g., hormonal agents, cytokines, interleukins, interferons, granulocyte colony stimulating factor (G-CSF), macrophage colony stimulating factor (M-CSF), granulocyte macrophage colony stimulating factor (GM-CSF), chemokines, or vaccine antigens), and/or anti-angiogenic agents (e.g., angiostatin or endostatin).

Other features and advantages of the invention will be apparent from the following detailed description and the claims.

DETAILED DESCRIPTION OF THE INVENTION

The invention provides methods for treating cancer, involving administration of a halichondrin B analog, such as an analog having the following structure:

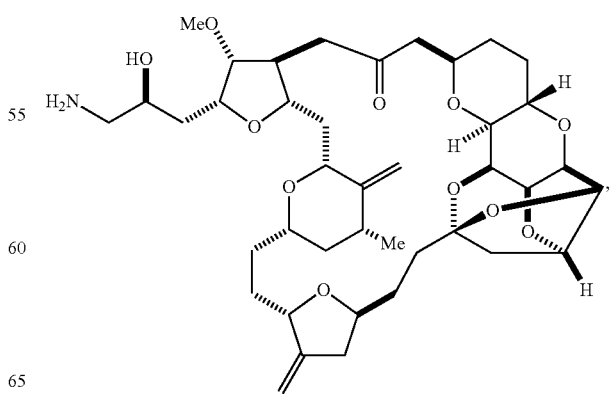

which is carried out in combination with a second approach to treatment. In addition to (or in place of) the compound noted above, any one or more of the halichondrin B analogs described in the patents noted above can be used in the invention.

There are numerous types of anti-cancer approaches that can be used in conjunction with halichondrin B analog treatment, according to the invention. These include, for example, treatment with chemotherapeutic agents (see below), biological agents (e.g., hormonal agents, cytokines (e.g., interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of a halichondrin B analog with these approaches. For example, if a drug is normally administered as a sole therapeutic agent, when combined with a halichondrin B analog, according to the invention, it may be desirable to decrease the dosage of the drug, as can be determined by those of skill in this art. Examples of the methods of the invention, as well as compositions and kits that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with halichondrin B treatment, according to the invention. Specific, non-limiting examples of these classes of drugs, as well as cancers that can be treated by their use, are as follows.

Antimetabolite drugs that halichondrin B analogs can be used with include, e.g., methotrexate, purine antagonists (e.g., mercaptopurine, thioguanine, fludarabine phosphate, cladribine, and pentostatin), and pyrimidine antagonists (e.g., gemcitabine, capecitabine, fluorouracil (e.g., 5-FU), floxuridine (FUdR; 2'-deoxy-5-fluoro-uridine; 5'-DFUR), cytarabine, and azacitidine). Use of these agents to treat particular types of cancers is well known in the art, and these agents can be used in combination with halichondrin B analogs to treat these and other types of cancers. As specific, non-limiting examples, a halichondrin B analog can be used with gemcitabine in the treatment of non-small cell lung carcinoma, pancreatic cancer, or metastatic breast cancer. In an additional example, a halichondrin B analog can be used in conjunction with capecitabine in the treatment of breast or colorectal cancers. In another example, floxuridine is used with a halichondrin B analog to treat breast cancer.

As is noted above, another class of chemotherapeutic drugs with which halichondrin B analogs can be used includes anticancer antibiotics. These include, for example, anthracyclines (e.g., doxorubicin, epirubicin, daunorubicin, and idarubicin), adriamycin, dactinomycin, idarubincin, plicamycin, mitomycin, and bleomycin. As with the drugs mentioned above, use of these agents to treat particular types of cancers is well known in the art, and they can be used in combination with halichondrin B analog treatment to treat these and other types of cancers. As a specific, non-limiting example, an anthracycline, such as doxorubicin, can be administered in conjunction with halichondrin B analog therapy for the treatment of breast or pancreatic cancers. Alternatively, a third agent, cyclophosphamide, can be used in this method.

Alkylating agents comprise another class of chemotherapeutic drugs that can be administered in conjunction with a halichondrin B analog, according to the invention. Examples of such drugs include procarbazine, dacarbazine, altretamine, cisplatin, carboplatin, and nitrosoureas. Halichondrin B analogs can be used with these agents in the treatment of cancers that these agents are known in the art to be used to treat, as well as in the treatment of other cancers. For example, a halichondrin B analog can be used in conjunction with carboplatinum in the treatment of non-small cell lung carcinoma or ovarian cancer.

An additional type of chemotherapeutic drug with which halichondrin B analogs can be administered, according to the invention, is plant alkaloids, such as vinblastine, vincristine, etoposide, teniposide, topotecan, irinotecan, vinorelbine, paclitaxel, and docetaxel. As specific, non-limiting examples, a halichondrin B analog can be used in conjunction with irinotecan for the treatment of colorectal cancer, or with topotecan in the treatment of ovarian or non-small cell lung cancers. In another example, a halichondrin B analog can be administered with vinorelbine in the treatment of breast cancer of non-small cell lung cancer.

Further types of anti-cancer agents that can be used in conjunction with halichondrin B analog treatment, according to the invention, are anticoagulants and antithrombotic agents. For example, heparin (e.g., low molecular weight heparin or heparin sulfate) or warfarin can be used. Use of these agents in treating patients by, for example, injection or oral administration, is well known in the art, and thus they can readily be adapted by those of skill in the art for use in the present invention.

Therapeutic antibodies can also be administered in conjunction with halichondrin B analog treatment, according to the invention. For example, antibodies (e.g., monoclonal antibodies) against tumor or cancer cell specific or enriched antigens can be used. As a specific example, antibodies against HER-2/erb B2, which is a protein that is overexpressed in breast cancer cells, can be used. Herceptin® (trastuzumab; Genentech, Inc.) is an example of a monoclonal antibody that is specific for HER-2/erb B2 that can be used in the invention.

Numerous approaches for administering anti-cancer drugs are known in the art, and can readily be adapted for use in the present invention. In the case of one or more drugs that are to be administered in conjunction with a halichondrin B analog, for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art.

Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug (or a subset of drugs).

As a specific, non-limiting example of a treatment regimen included in the invention, a halichondrin B analog (e.g., 0.01-5 mg/m$^2$) can be administered to a patient by intravenous infusion for 0.5-3 hours, followed by intravenous infusion of another drug (e.g., gemcitabine, e.g., 500-900 mg/m$^2$) for 0.5-3 hours. This course of treatment can be repeated every 2-3 weeks, as determined to be tolerable and effective by those of skill in the art. In a variation of this method, the treatment is carried out with both drugs on the first day, as is noted above, but then is followed up with treatment using only the secondary drug (e.g., gemcitabine) in ensuing weeks.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

In addition to the cancers mentioned above, the methods and compositions of the invention can be used to treat the following types of cancers, as well as others: skin (e.g., squamous cell carcinoma, basal cell carcinoma, or melanoma), prostate, brain and nervous system, head and neck, testicular, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Other types of cancers that can be treated using the methods of the invention include fibrosarcoma, neurectodermal tumor, mesothelioma, epidermoid carcinoma, and Kaposi's sarcoma.

The invention also includes compositions that include a halichondrin B analog in combination with an additional therapeutic agent(s), such as any of those agents listed above. The drugs in these compositions preferably are formulated for administration to patients (e.g., in physiological saline) or, alternatively, can be in a form requiring further processing prior to administration. For example, the compositions can include the drugs in a lyophilized form or in a concentrated form requiring dilution. Formulation of drugs for use in chemotherapeutic methods can be carried out using standard methods in the art (see, e.g., *Remington's Pharmaceutical Sciences* (18$^{th}$ edition), ed. A. Gennaro, 1990, Mack Publishing Co., Easton, Pa.).

Also included in the invention are kits that include one or more halichondrin B analogs and one or more additional anti-cancer agents, as is discussed above. The halichondrin B analog(s) and additional anti-cancer agent(s) can be present in a single container, such as a vial, or can be present in separate containers. Further, the different agents can be present in forms that are ready for administration or forms requiring further formulation (e.g., lyophilized form). The kits can also include diluents for the agents, instructions for administration of the agents, one or more labels listing the contents of the kits, and/or devices used in agent administration.

The disclosed compound has pharmacological activity, including anti-tumor and anti-mitotic activity, as demonstrated in section D of U.S. Pat. No. 6,214,865. Examples of tumors include melanoma, fibrosarcoma, monocytic leukemia, colon carcinoma, ovarian carcinoma, breast carcinoma, osteosarcoma, prostate carcinoma, lung carcinoma and ras-transformed fibroblasts.

The invention features pharmaceutical compositions that include a compound of formula (I) (see U.S. Pat. No. 6,214,865 for formula (I)) and a pharmaceutically-acceptable carrier. Compositions can also include a combination of disclosed compounds, or a combination of one or more disclosed compounds and other pharmaceutically-active agents, such as an anti-tumor agent, an immune-stimulating agent, an interferon, a cytokine, an anti-MDR agent or an anti-angiogenesis agent. Compositions can be formulated for oral, topical, parenteral, intravenous, or intramuscular administration, or administration by injection or inhalation. Formulations can also be prepared for controlled-release, including transdermal patches.

A method for inhibiting tumor growth in a patient includes the step of administering to the patient an effective, anti-tumor amount of a disclosed compound or composition. The invention also contemplates combination therapies, including methods of co-administering a compound of formula (I) (see U.S. Pat. No. 6,214,865 for formula (I)) before, during, or after administering another pharmaceutically active agent. The methods of administration may be the same or different. Inhibition of tumor growth includes a growth of the cell or tissue exposed to the test compound that is at least 20% less, and preferably 30%, 50%, or 75% less than the growth of the control (absence of known inhibitor or test compound).

What is claimed is:

1. A method of inhibiting growth of a tumor in a patient, said method comprising administering to said patient a compound of the structure:

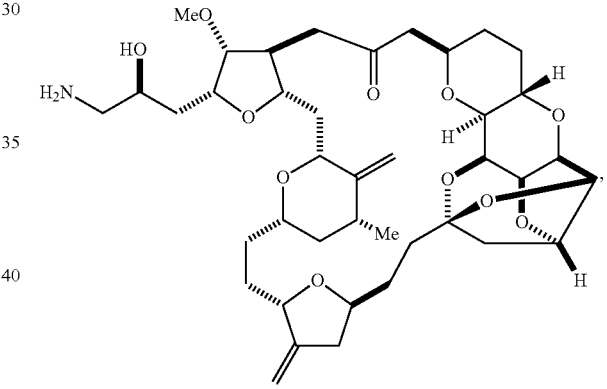

or a pharmaceutically acceptable salt thereof, wherein said tumor is breast carcinoma, and wherein said compound or pharmaceutically acceptable salt is not co-administered with another pharmaceutically active agent.

2. The method of claim 1, wherein said compound or pharmaceutically acceptable salt is administered in a pharmaceutical composition comprising a pharmaceutically-acceptable carrier.

3. The method of claim 1, wherein said compound or pharmaceutically acceptable salt is administered by oral, topical, parenteral, or intravenous routes, or by injection or inhalation.

4. The method of claim 1, wherein said compound or pharmaceutically acceptable salt is administered in a controlled-release formulation.

5. The method of claim 1, wherein said method consists of administration of said compound or pharmaceutically acceptable salt, in a pharmaceutically acceptable carrier or diluent, to said patient.

* * * * *